(12) United States Patent
Kim et al.

(10) Patent No.: US 6,768,014 B2
(45) Date of Patent: Jul. 27, 2004

(54) PROCESS FOR PREPARING 17α-ACETOXY-11β-[4-N,N(DIMETHYLAMINO)PHENYL]-21-METHOXY-19-NORPREGNA-4,9-DIENE-3,20-DIONE, INTERMEDIATES USEFUL IN THE PROCESS, AND PROCESSES FOR PREPARING SUCH INTERMEDIATES

(75) Inventors: Hyun Koo Kim, Bethesda, MD (US); Pemmaraju N. Rao, San Antonio, TX (US); James W. Cessac, San Antonio, TX (US); Anne Marie Simmons, San Antonio, TX (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 84 days.

(21) Appl. No.: 10/169,139
(22) PCT Filed: Dec. 29, 2000
(86) PCT No.: PCT/US00/35479
§ 371 (c)(1),
(2), (4) Date: Jun. 27, 2002
(87) PCT Pub. No.: WO01/47945
PCT Pub. Date: Jul. 5, 2001

(65) Prior Publication Data
US 2003/0060646 A1 Mar. 27, 2003

Related U.S. Application Data
(60) Provisional application No. 60/173,470, filed on Dec. 29, 1999.

(51) Int. Cl.[7] .................................................. C07J 5/00
(52) U.S. Cl. ..................................................... 552/595
(58) Field of Search ........................................ 552/595

(56) References Cited
U.S. PATENT DOCUMENTS

| | | |
|---|---|---|
| 3,314,976 A | 4/1967 | Hewett et al. |
| 3,496,199 A | 2/1970 | Uskokovic |
| 3,956,316 A | 5/1976 | Uskokovic et al. |
| 4,511,511 A | 4/1985 | Lewbart |

FOREIGN PATENT DOCUMENTS

| | | |
|---|---|---|
| EP | 658 533 | 6/1995 |
| WO | WO 97/41145 | 11/1997 |

OTHER PUBLICATIONS

Teutsch et al.; "Synthesis of 11β–Vinyl–19–Norsteriods As Potent Progestins", *Elsevier Science Publishers*, vol. 39, No. 6, New York, NY, pp. 607–615, (Jun. 1, 1982).

*Primary Examiner*—Barbara P. Badio
(74) *Attorney, Agent, or Firm*—Leydig, Voit & Mayer, Ltd.

(57) ABSTRACT

A compound having general formula (I) in which $R^1$ is a member selected from the group consisting of $-OCH_3$, $-SCH_3$, $-N(CH_3)_2$, $-NHCH_3$, $-CHO$, $-COCH_3$ and $-CHOHCH_3$; $R^2$ is a member selected from the group consisting of halogen, alkyl, acyl, hydroxy, alkoxy, acyloxy, alkyl carbonate, cypionyloxy, S-alkyl and S-acyl; $R^3$ is a member selected from the group consisting of alkyl, hydroxy, alkoxy and acyloxy; $R^4$ is a member selected from the group consisting of hydrogen and alkyl; and X is a member selected from the group consisting of $-O$ and $-N-OR^5$, wherein $R^5$ is a member selected from the group consisting of hydrogen and alkyl. In addition to providing the compounds of formula (I), the present invention provides methods wherein the compounds of formula (I) are advantageously used, inter alia, to antagonize endogenous progesterone; to induce menses; to treat endometriosis; to treat dysmenorrhea; to treat endocrine hormone-dependent tumors; to treat uterine fibroids; to inhibit uterine endometrial proliferation; to induce labor; and for contraception.

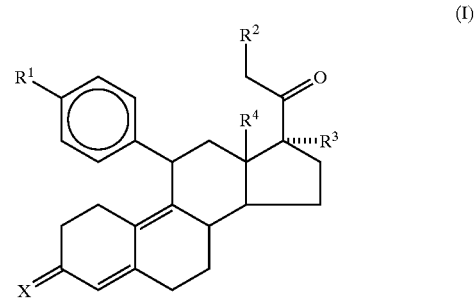

(I)

8 Claims, 2 Drawing Sheets

PROCESS FOR PREPARING 17α-ACETOXY-11β-[4-N,N(DIMETHYLAMINO)PHENYL]-21-METHOXY-19-NORPREGNA-4,9-DIENE-3,20-DIONE, INTERMEDIATES USEFUL IN THE PROCESS, AND PROCESSES FOR PREPARING SUCH INTERMEDIATES

CROSS-REFERENCE TO A RELATED APPLICATION

This application is the national stage of PCT/US00/35479, filed Dec. 29, 2000 which claims the benefit of U.S. provisional patent application No. 60/173,470, filed Dec. 29, 1999, the disclosure of which is incorporated by reference in its entirety.

TECHNICAL FIELD OF THE INVENTION

The present invention relates generally to steroids, and in particular to a process for preparing 17α-acetoxy-11β-[4-N,N-(dimethylamino)phenyl]-21-methoxy-19-norpregna-4,9-diene-3,20-dione, intermediates useful in the process, and processes for preparing such intermediates.

BACKGROUND OF THE INVENTION

International patent application No. PCT/US 97/07373, filed Apr. 30, 1997, WO 97/41145, published Nov. 6, 1997, and U.S. provisional patent application No. 60/016,628, filed May 1, 1996, both assigned to the same assignee as the present application, disclose, inter alia, 17α-acetoxy-11β-[4-N,N-(dimethylamino)phenyl]-21-methoxy-19-norpregna-4,9-diene-3,20-dione as an antiprogestational agent. This compound also is useful in other treatments, e.g., to induce menses or labor, to treat diseases such as endometriosis, dysmenorrhea, and endocrine hormone-dependent tumors, uterine fibroids, and to inhibit uterine endometrial proliferation.

Figure 1:
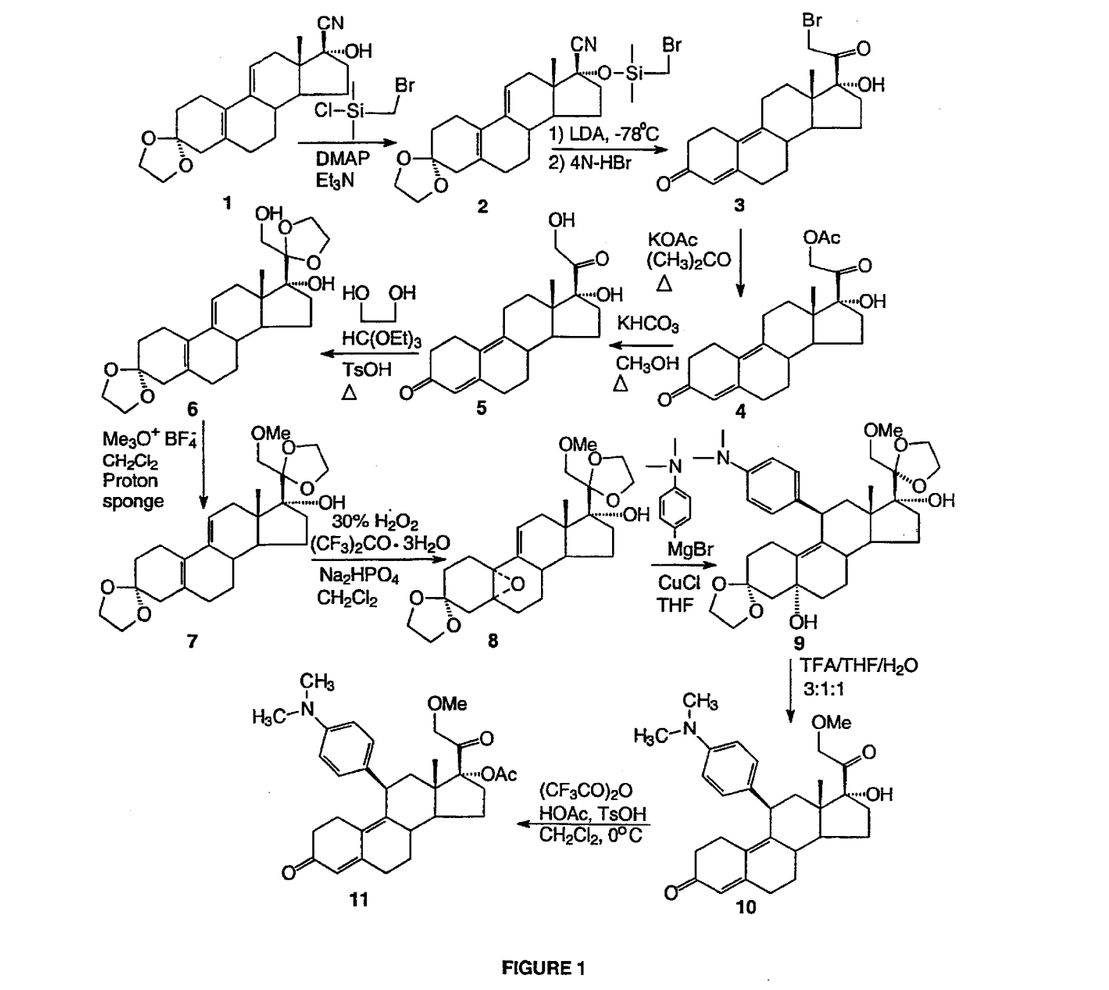
FIG. 1 sets forth a process for preparing the compound of formula 11 as described in application Ser. No. 60/016,628.

The '628 application discloses a method for preparing this compound, the method being outlined in FIG. 1 herein. As shown in FIG. 1, the cyanohydrin ketal (1) was converted to the silyl ether (2) by reaction with bromomethyldimethylsilyl chloride. Subsequent treatment with lithium diisopropylamide gave the 17α-hydroxy-21-bromo derivative (3). Displacement of the 21-bromo substituent by acetate was effected by refluxing with potassium acetate in acetone to produce the 21-acetate (4). Hydrolysis of the crude 21-acetate (4) by potassium bicarbonate gave the 17α,21-diol (5). Ketalization of the 17,21-diol-4,9-diene-3,20-dione (5) was achieved by reaction with ethylene glycol and tosic acid with water being removed by in vacuo azeotropic distillation. This produced the diketal (6). The less-hindered 21-hydroxyl group was selectively methylated with trimethyloxonium tetrafluoroborate using 1,8-bis(dimethylamino)-naphthalene as a base to provide the 21-methoxy compound (7).

Epoxidation of the 21-methoxy compound (7) with hexafluoroacetone trihydrate and 30% hydrogen peroxide produce a 2:1 mixture of 5α,10α- and 5β,10β-epoxides (8) as evidenced by NMR. As attempts to isolate pure 5α,10α-epoxide (8) were unsuccessful, the crude mixture was used directly on to the copper (I) catalyzed Grignard reaction, to obtain the 11β-[4-(N,N-dimethylamino)phenyl] derivative (9). Hydrolysis with trifluoroacetic acid restored the 4,9-diene-3,20-dione structure (10). Acetylation of the 17α-hydroxy compound (10) with the mixed anhydride formed from trifluoroacetic anhydride and acetic acid afforded the desired 19-norprogesterone compound (11).

While the method described in the '628 application is satisfactory to produce the desired compound 11, there nevertheless remains a desire to provide a process for increasing the product yield. There further exists a desire for a process that employs reagents which need not be used in a large excess. There further exists a desire for a process that uses less expensive or safer reagents or conditions.

The advantages of the present invention, as well as additional inventive features, will be apparent from the description of the invention provided herein.

BRIEF SUMMARY OF THE INVENTION

Figure 2:
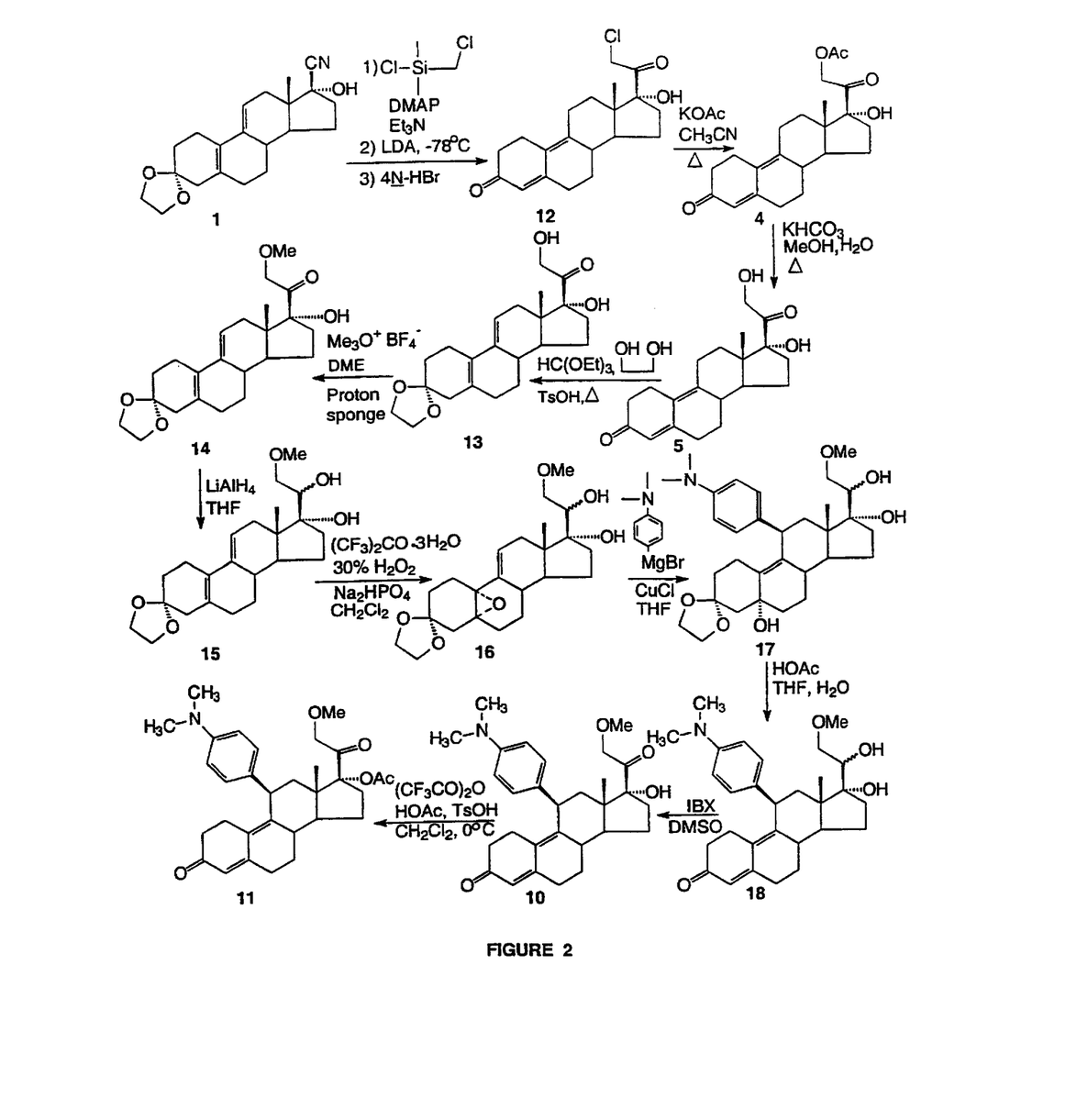
FIG. 2 sets forth a process for preparing the compound of formula 11 in accordance with a preferred embodiment of the present invention.

The present invention provides a process for preparing the compound of formula 11, that is, 17α-acetoxy-11β-[4-N,N-(dimethylamino)phenyl]-21-methoxy-19-norpregna-4,9-diene-3,20-dione, e.g., as shown in FIG. 2. The process of the present invention includes (a) replacing the cyanohydrin group of the compound of formula 1 with a 17-β-chloroacetyl group-17-α-hydroxyl group to obtain the compound of formula 12; (b) displacing the chloro group of the compound of formula 12 by an acetoxy group to obtain the compound of formula 4; (c) deacetylating the compound of formula 4 to obtain the compound of formula 5; (d) selectively ketalizing the compound of formula 5 to obtain the compound of formula 13; (e) selectively methylating the 21-hydroxyl group of the compound of formula 13 to obtain the compound of formula 14; (f) reducing the 20-ketone group of the compound of formula 14 to obtain the compound of formula 15; (g) epoxidizing the compound of formula 15 to obtain the 5α,10α-compound of formula 16; (h) introducing a N,N-dimethylaminophenyl group at the 11β-position and concomitantly opening the epoxide ring of the compound of formula 16 to obtain the compound of formula 17; (i) deketalizing the compound of formula 17 to obtain the compound of formula 18; (j) selectively oxidizing the 20-hydroxyl group of the compound of formula 18 to a ketone group to obtain the compound of formula 10; and (k) acetylating the compound of formula 10 to obtain the compound of formula 11.

The process of the present invention has one or more advantages, e.g., it employs smaller quantities of or less expensive solvents and/or reagents. The process involves intermediates, reagents, or byproducts which are relatively safe to handle and to dispose of, and/or that are more efficiently used in the synthesis of the compound of formula 11. The process also provides the desired final compound as well as intermediates in relatively high quantities and purity levels. For example, an overall yield of from about 5 to about 6 percent or more can be achieved in preparing the compound of formula 11 starting from the compound of formula 1 using the process of the present invention. The process also involves purification methodologies that are easier to practice in a large scale compared to methods such as chromatography or distillation methodologies used heretofore. The process further involves less toxic reagents. One or more intermediates can be isolated upon evaporation of volatile solvents followed by aqueous precipitation. The process is less labor intensive and is scalable.

The present invention further provides novel intermediates useful in preparing the compound of formula 11. These intermediates include the compounds of formulae 12–18. The present invention further provides processes for preparing these intermediates. The present invention further provides a process for selectively oxidizing the secondary alcohol group of a composition containing secondary and tertiary alcohol groups. The selective oxidation process comprises treating the composition with a haloxybenzoic acid.

While the invention has been described and disclosed below in connection with certain preferred embodiments and procedures, it is not intended to limit the invention to those specific embodiments. Rather it is intended to cover all such alternative embodiments and modifications as fall within the spirit and scope of the appended claims.

DETAILED DESCRIPTION OF EMBODIMENTS OF THE INVENTION

In one aspect, the present invention provides a process for preparing the compound of formula 11 generally, and preferably in accordance with the schematic shown in FIG. 2.

The starting material, the cyanohydrin compound of formula 1, can be obtained commercially, for example, from Davos Chemical Inc. in New Jersey. In accordance with a preferred embodiment of the invention, the starting material is first reacted with chloro(chloromethyl)dimethylsilane to form a 17-O-silylated derivative which is then converted to a 17-chloroacetyl compound with the 17α-hydroxyl group being maintained.

The silylation reaction is preferably carried out in the presence of at least one base to scavenge the acid by-product. Examples of suitable bases include tertiary amines such as trialkylamines, pyridines, and dialkylaminopyridines, as well as combinations thereof, with the preferred base being a mixture of 4-dimethylaminopyridine (DMAP) and triethylamine. Advantageously, DMAP can be used in a sub-stoichiometric amount when DMAP and another base are used. The reaction is preferably carried out in a dry solvent such as anhydrous solvent. Examples of solvents suitable for carrying out the reaction include tetrahydrofuran (THF), diethyl ether, acetonitrile, dichloromethane, dioxane, dioxolane, and the like, with THF being a preferred solvent. During the reaction, the reaction mixture is advantageously maintained at a temperature of from about −78° C. to about 0° C., and preferably at a temperature of about −78° C.

The resulting 17-O-silylated derivative is then reacted, preferably in a one-pot process, with an alkali metal dialkylamide, to convert the cyanohydrin group to a 17α-hydroxy-17β-chloroacetyl group. The conversion of the cyanohydrin group is preferably carried out by the procedure known as the Silicon Nucleophilic Annelation Process (SNAP). See Livingston et al., *Adv. Med. Chem.*, 1, 137–174 (1992); Livingston et al., *J. Amer. Chem. Soc.*, 112, 6449–50 (1990); and U.S. Pat. Nos. 4,921,638 and 4,977,255. Examples of suitable alkali metals of the dialkylamide include lithium, sodium, potassium, and rubidium, with lithium being preferred. The SNAP reaction is carried out at low temperatures, preferably at or below about −78° C. Lithium diisopropylamide is a preferred reagent for the formation of α-silyl carbanion.

The SNAP reaction, it is believed, results in the formation of an α-silyl carbanion which attacks the cyano group intramolecularly to provide an intermediate silacycle. Subsequent hydrolysis of the intermediate provides the 17β-chloroacetyl compound of formula 12 with a hydroxyl group at the 17α-position. The hydrolysis can be carried out by any suitable method, for example, by the use of an acid, preferably in excess relative to the base employed in the reaction. Preferred examples of suitable acids include HCl and HBr. The acid is preferably added to the reaction mixture as a 4-Normal solution in water. By carrying out the above reaction as a one-pot procedure in accordance with a preferred embodiment of the invention, it is possible to eliminate difficult or cumbersome isolation procedures such as chromatographic isolation of the halomethylsilyl ether. Any problems associated with chemical instability of the halomethylsilyl ether can be avoided. In addition, the one-pot procedure offers increased product yield, e.g., an yield of about 95% or more. However, it will be appreciated by those skilled in the art that it is not essential to the process of the present invention that a one-pot procedure be utilized.

The compound of formula 12 is preferably converted to the compound of formula 4 by displacing the chloro group with an acetoxy group. The displacement is carried out by any suitable method, for example, by reacting the chloro compound with an acetate such as alkali metal acetate. The acetate is preferably employed in excess relative to the chloro group. The reaction can be carried out by heating the compound of formula 12 with potassium acetate in a suitable solvent, e.g., acetonitrile. The precipitated KCl is removed by filtration, and the product isolated from the reaction mixture by distilling off the solvent, followed by taking up the residue in a solvent such as methylene chloride and extracting the methylene chloride solution with water. The acetate is found in the organic phase. The acetate can be recovered by evaporating the solvent.

The compound of formula 4 is then converted to the compound of formula 5 by hydrolyzing the acetoxy group to a hydroxyl group. The deacetylation is carried out by hydrolyzing the compound of formula 4 with a suitable hydrolytic agent, e.g., a weak base such as a bicarbonate. A suitable bicarbonate is potassium bicarbonate. The hydrolysis can be carried out by heating, preferably refluxing, a methanol solution of the compound of formula 4 with potassium bicarbonate. The product is isolated from the reaction mixture by distilling off the solvent, followed by taking up the residue in a solvent such as methylene chloride and extracting the methylene chloride solution with water. The compound of formula 5 is found in the organic phase. The compound can be recovered by removing, e.g., by evaporation, the solvent. The compound of formula 5 is obtained in high yields, e.g., an yield of about 92% or more.

The 3-ketone group of the compound of formula 5 is selectively ketalized, leaving the 20-ketone group intact. Thus, the selective ketalization converts the 3-ketone to a ketal group in preference to the 20-ketone group. For example, at least 80% of the ketalization proceeds at the 3-position, preferably at about 83% or more, and more preferably only or quantitatively at the 3-postion.

The selective ketalization can be carried out by methods known to those skilled in the art. For example, the compound of formula 5 can be reacted with a glycol such as ethylene glycol, triethylorthoformate, and a suitable catalyst, for example, an acid catalyst such as p-toluenesulfonic acid. The selective ketalization of the 3-ketone group proceeds at mild reaction conditions, for example, at a temperature of below about 30° C. An advantage of the process of the present invention is that it eliminates the need for ketalizing the 20-ketone group, as ketalization of the 20-ketone group generally involves forcing conditions such as high temperatures and pressures. The process of the present invention also has the advantage that it eliminates the need for the tedious vacuum azeotropic distillation involved in the preparation of the 3,20-diketal as well as a later deketalization involving the use of trifluoroacetic acid; see, e.g., FIG. 1.

The 21-hydroxyl group of the compound of formula 13 is then selectively methylated to form the compound of formula 14. The selective methylation can be carried out by any suitable method, preferably by the use of trimethyloxonium salt such as trimethyloxonium tetrafluoroborate as the methylating agent. An advantage of this methylating agent is that the compound of formula 14 can be obtained in essentially quantitative yield by the use of only four equivalents of the methylating agent per equivalent of the hydroxyl group. The stereochemistry at the 17-carbon is preserved. The selective methylation proceeds preferentially at the 21-position, at least 80% at the 21-position, preferably at an yield of about 92% or more, and more preferably, only or quantitatively at the 21-position. Any suitable solvent can be used to carry out the selective methylation reaction. Preferably an ether solvent, and more preferably dimethoxyethane, is used to carry out the reaction. The reaction is advantageously carried out by using a proton sponge such as a sterically hindered and less nucleophilic base, e.g., 1,8-bis (dimethylamino)-naphthalene (Evans, D A, Ratz A M, Huff, B E and Sheppard, G S (1995), *J. Am. Chem. Soc.*, 117, 3448–3467). The proton sponge is preferably used in excess, more preferably at about four equivalents per equivalent of the hydroxyl group being methylated. The reaction can be carried out at moderate or ambient temperatures, e.g., below about 30° C., such as at about 25° C.

The 20-ketone group of the compound of formula 14 is then protected, e.g., by reducing it to a hydroxyl group. The reduction can be preferably carried out by treating the compound with a hydride such as a metal hydride, preferably lithium aluminum hydride. The resulting major product of the compound of formula 15 can be purified by crystallization, e.g., from an ether such as diethyl ether, isopropyl ether, isobutyl ether, n-butyl ether, with diethyl ether being preferred. Any small amount of the second isomer that may form can be thus removed. The compound of formula 15 is obtained in good yields, e.g., greater than about 58% or more of the major isomer. As the minor isomer can be recycled (e.g., oxidized back to the compound of formula 14), loss of the intermediate is minimal.

The compound of formula 15 is preferably epoxidized to obtain the compound of formula 16. The epoxidation can be carried out by methods known to those skilled in the art. The epoxidation is advantageously carried out by reacting the compound of formula 15 with an adduct formed from the reaction of a halogenated ketone such as acetone and a peroxide in the presence of a weak base such as a phosphate. Any suitable peroxide may be used, including hydrogen peroxide, sodium peroxide, potassium peroxide, benzoyl peroxide, and acetyl peroxide, with hydrogen peroxide being preferred. A convenient source of hydrogen peroxide is the 30 wt % solution in water which is available commercially.

The halogenated ketone is preferably a hexahalogenated ketone, e.g., a hexachloro-, hexabromo-, or hexafluoroacetone, with hexafluoroacetone being preferred. The phosphate can be an alkali or alkaline earth metal phosphate. A preferred example of a suitable phosphate is $Na_2HPO_4$. Especially preferred is the use of $Na_2HPO_4$ in combination with 30 wt % hydrogen peroxide solution and hexafluoroacetone. The epoxidation is carried out in a suitable solvent, e.g., a halogenated solvent. Examples of halogenated solvents include chloroform, methylene chloride, dichloroethane, trichloroethane, with methylene chloride being a preferred solvent.

Epoxidation of the compound of formula 15 is particularly advantageous as the $5\alpha,10\alpha$-epoxide can be formed in preference to the less desirable $5\beta,10\beta$-epoxide. Thus, the compound of formula 16 can be prepared so that the ratio of the $5\alpha,10\alpha$-epoxide to the $5\beta,10\beta$-epoxide is greater than 2:1, and preferably 3:1 or greater. The pure $5\alpha,10\alpha$-epoxide can be advantageously obtained by trituration of the mixture with ether.

The epoxide ring of the compound of formula 16 can be concomitantly opened along with the conjugate addition of a N,N-dimethylaminophenyl Grignard reagent at the 11β-position in the presence of a cuprous salt, e.g., cuprous chloride. The Grignard reagent can be prepared in situ from magnesium metal, a 4-halo-N,N-dimethylaniline, e.g., 4-bromo-N,N-dimethylaniline, and a crystal of iodine. The reaction can be carried out in a suitable solvent such as an ether, preferably tetrahydrofuran.

The Grignard reaction is carried out preferably in a dry vessel. To a reaction vessel containing the desired amount of magnesium, a small crystal of iodine is added, and the dried solvent is added to the vessel. A few drops of 1,2-dibromoethane are added to facilitate the initiation of the Grignard reaction. A solution of the 4-halodimethylaniline is then added. The reaction mixture is then heated to initiate the Grignard reaction, as evidenced by the bleaching of color and consumption of iodine. To the reaction mixture is then added the cuprous salt. To the stirred mixture is added the epoxide. The reaction mixture is quenched by the addition of an ammonium salt, e.g., ammonium chloride or bromide, solution in water. The cuprous ion is then oxidized. Any suitable oxidizing agent, e.g., air or oxygen, can be employed to carried out the oxidation. The resulting compound of formula 17 can be isolated by extraction into an organic medium such as ether.

The use of the purified $5\alpha,10\alpha$ form of the compound of formula 16 allows the use of less amount of the valuable Grignard reagent compared to when a crude mixture of the $5\alpha,10\alpha$ and $5\beta,10\beta$-epoxides is used. In addition, the use of the purified $5\alpha,10\alpha$ epoxide eliminates the need for a chromatographic purification of the 11β-substituted Grignard product.

The compound of formula 17 is then deketalized to obtain the compound of formula 18. The removal of the ethylenedioxy group can be carried out by the use of an acid such as an organic acid. A preferred organic acid is acetic acid. The secondary alcohol, the 20-hydroxyl group, of the compound of formula 18 which also contains a tertiary alcohol group at C17 can be selectively oxidized to obtain the compound of formula 10. By the selective oxidation, the 21-hydroxyl group is preferentially oxidized, e.g., at least 80% of the oxidation takes place at the 21-position. Preferably, the oxidation takes place only or quantitatively at the 21-position, leaving the 17α-tertiary alcohol group essentially intact. The selective oxidation can be carried out by the use of a suitable oxidizing agent, e.g., a haloxyacid such as 2-iodoxybenzoic acid.

The compound of formula 10 can be acetylated at the 17-position to obtain the compound of formula 11. The acetylation can be carried out by the use of any acetylating agent, preferably a combination of trifluoroacetic anhydride, acetic acid, and p-toluenesulfonic acid.

The following Examples further illustrate the present invention, but of course should not be construed in any way as limiting the scope of the invention.

EXAMPLE 1

Preparation of 17α-hydroxy-21-chloro-19-norpregna-4,9-diene-3,20-dione (12):

The cyanohydrin (1, 50 g, 146.43 mmol; dried over $P_2O_5$) was suspended in 550 mL of dry THF and stirred mechanically at room temperature under nitrogen. 4-(Dimethylamino)pyridine (DMAP) (4.47 g, 36.61 mmol) was added as a solid. 26.7 mL (197.68 mmol) of freshly distilled triethylamine (TEA) (27.6 mL, 197.68 mmol) was added via syringe followed by the addition of freshly distilled chloro(chloromethyl)-dimethylsilane (23.0 mL, 174.72 mmol). The reaction mixture was allowed to stir overnight at ambient temperature. Thin layer chromatography (TLC)(on silica; 2% acetone in methylene chloride) showed that all the starting material had been converted to the silyl ether.

The reaction mixture was then cooled to −78° C. and diluted with THF (800 mL). Lithium diisopropylamide (LDA) (2.0 M in THF/heptane, 225 mL, 450 mmol) was added drop wise to the reaction mixture via an additional funnel over a period of ½ hr. Upon completion of the addition, the reaction mixture was stirred for a period of 2 hr at −78° C. in a dry ice bath. 4 N HCl (1000 mL, 4 moles) was added via the addition funnel, the dry ice bath was removed, and the reaction mixture allowed to stir overnight at room temperature. TLC (silica; 5% acetone in methylene chloride) indicated that the reaction had gone to completion.

The reaction mixture was then cooled to 0° C. in an ice bath and neutralized by the addition of concentrated $NH_4OH$ (270 mL, 4 mols). The mixture was transferred to a separatory funnel and extracted with EtOAc (3×). The organic fractions were washed with water (2×), and then with brine (1×). The combined EtOAc fractions (3×) were filtered through sodium sulfate and evaporated in vacuo. The resulting solid was taken up in hot methylene chloride/ethyl acetate (about 2 L), and the resulting solution was filtered to remove a fine gray precipitate. Evaporation of the filtrate provided a yellow solid. The solid was triturated with ether and collected on a Buchner funnel. The solid was then washed with additional ether and dried overnight in vacuo to recover 40.28 g of the 21-chloro compound (12) in 78.9% yield. This material was suitable to carry directly on to the next reaction.

A small portion of the compound was crystallized from hot isopropanol, then dried over toluene in vacuo for analysis; m.p.=191–193° C. FTIR (KBr, diffuse reflectance): $V_{max}$ 3436, 2948, 1729, 1644, 1599, 1572, 1444, 1392, 1280 ad 1223 $cm^{-1}$. NMR (300 MHZ, $CDCl_3$) : δ 0.836 (s, 3 H, C18-$CH_3$), 4.348 and 4.647 (AB, 2 H, C21-$CH_2$, $J_{AB}$=16.66 Hz) and 5.691 (s, 1 H, C4-CH). MS (EI) m/z (relative intensity): 348 (M+, 100.0), 313 (32.9), 253 (67.1), 228 (54.4), 213 (71.5) and 91 (55.4).

Preparation of 17α-hydroxy-21-acetoxy-19-norpregna-4,9-diene-3,20-dione (4):

A suspension of the 21-chloro compound (12, 40 g, 114.66 mmol) and KOAc (117.78 g, 1.20 moles) in acetonitrile (900 mL) was stirred mechanically and brought to reflux under nitrogen. After 1 hr reaction, TLC (silica; 5% acetone in methylene chloride) indicated that the reaction had gone to completion. The reaction mixture was allowed to cool to room temperature and the precipitated KCl and the excess KOAc were removed by filtration through a sintered glass funnel. The acetonitrile was evaporated in vacuo, and the resulting residue was taken up in methylene chloride and water. The mixture was transferred to a separatory funnel, the organic and the aqueous layers were allowed to separate, and the organic layer was removed, washed with water, and then with brine. The combined methylene chloride extracts (3×) were filtered through sodium sulfate and evaporated in vacuo. The resulting pale yellow solid was dried overnight under vacuum to recover 35.35 g of the crude 21-OAc (4) in 82.8% yield. The material (4) was of sufficient purity to carry on to the hydrolysis reaction later.

A sample of analytical purity was obtained by crystallization of a small amount of 4 from boiling acetone. The sample was dried under vacuum over toluene; m.p. 216–222° C. FTIR (KBr, diffuse reflectance): $v_{max}$ 3470, 2947, 1744, 1720, 1642, 1606, 1367 and 1236 $cm^{-1}$. NMR (300 MHZ, $CDCl_3$): δ 0.844 (s, 3 H, C18-$CH_3$), 2.183 (s, 3 H, C21-OAc), 4.863 and 5.074 (AB, 2 H, C21-$CH_2$, $J_{AB}$=17.56 Hz) and 5.686 (s, 1 H, C4-CH). MS (EI) m/z (relative intensity): 372 ($M^+$, 86.1), 312 (74.9), 271 (74.5), 253 (100.0), 213 (93.3), 162 (76.2) and 91 (57.7).

Preparation of 17α,21-dihydroxy-19-norpregna-4,9-diene-3,20-dione (5):

A suspension of the crude 21-acetate (4, 34.57 g, 92.9 mmol) in a freshly opened methanol solvent was deoxygenated by sparging with nitrogen for ½ hr. A 0.5 M aqueous solution of $KHCO_3$ was similarly deoxygenated. A $KHCO_3$ solution (280 mL, 140 mmol=1.5×) was added to 4, and the suspension was stirred mechanistically and brought to reflux under nitrogen, whereupon a solution formed. After ½ hr at reflux, TLC (silica; 5% isopropanol in methylene chloride) indicated that all starting material had been converted to a single, more polar product. The reaction mixture was cooled to room temperature, then neutralized by the addition of HOAc (8.0 mL, 140 mmol). The methanol was evaporated in vacuo. Methylene chloride was added to the residue obtained, along with more water, and the mixture was transferred to a separatory funnel. The organic and aqueous layers were allowed to separate. The organic layer was separated, washed again with water, and then with brine. The combined methylene chloride extracts (3×) were filtered through sodium sulfate and evaporated in vacuo. The resulting solid was dried under high vacuum to recover 29.20 g of a yellow solid (5) in 95.2% yield.

A small amount of 5 was crystallized from a minimum amount of boiling methanol to afford pale yellow crystals. It was dried in vacuo at 111° C. for analysis: m.p. 197–201° C. FTIR (KBr, diffuse reflectance): $v_{max}$ 3520, 2944, 2865, 1714, 1654, 1597, 1577 and 1387 $cm^{-1}$. NMR (300 MHz, $CDCl_3$): δ 0.820 (s, 3 H, C18-$CH_3$), 4.320 and 4.695 (AB, 2 H, C21-$CH_2$, $J_{AB}$=19.81 Hz) and 5.676 (s, 1 H, C4-CH). MS (EI) m/z (relative intensity): 330 ($M^+$, 100.0), 271 (37.3), 253 (54.2), 228 (64.9), 213 (63.2), 74 (27.2) and 91 (43.3).

Preparation of 3,3-Ethylenedioxy-17α,21-dihydroxy-19-norpregna-5(10),9(11)-dien-20-one (13):

The 17α,21-diol (5, 10.0 g, 30.29 mmol) was suspended in methylene chloride (100 mL, freshly opened) and stirred magnetically at room temperature under nitrogen. Freshly distilled triethylorthoformate (12.6 mL, 75.73 mmol) was added via syringe, followed by ethylene glycol (8.81 mL, 158.11 mmol). A solution formed almost immediately. Tosic acid (287 mg, 1.1 mmol) was added as a solid and stirring continued for ½ hr. At that time, TLC (silica; 5% isopropanol in methylene chloride) indicated all starting material had been converted to a single polar product. The reaction mixture was transferred to a separatory funnel and washed with saturated $NaHCO_3$ (1×), water (1×) and brine (1×). Combined methylene chloride extracts (3×) were dried by filtration through sodium sulfate and evaporated in vacuo to give a pale yellow solid. The solid was triturated with ether, collected on a Buchner funnel, and dried overnight under high vacuum to afford 9.19 g of 13 as a pale beige powder in 81% yield.

A small amount of material (13) was reserved, crystallized from a minimum amount of hot methylene chloride, and dried in vacuo at 111° C. to recover 198 mg of white crystals; m.p.=214–216° C. FTIR (KBr, diffuse reflectance): $v_{max}$ 3481, 3399, 3046, 2924, 2878, 2843, 1714, 1471, 1389, 1368, 1263, 1229 and 1157 cm$^{-1}$. NMR (300 MHZ, CDCl$_3$): δ 0.637 (s, 3 H, C18-CH$_3$), 3.985 (s, 4 H, C3-OCH$_2$CH$_2$O—), 4.293 (dd, 1 H, C21-CH, J$_1$=19.81, J$_2$=3.60 Hz,), 4.697 (dd, 1 H, C21-CH, J$_1$=19.81, J$_2$=3.60 Hz,), and 5.567 (t, 1 H, J=2.40, C11-CH=). MS (EI) m/z (relative intensity): 374 (M$^+$, 51.7), 356 (21.4), 297 (34.9), 169 (54.9), 99 (98.6), and 86 (100). Anal. Calcd. for C$_{22}$H$_{30}$O$_5$.CH$_2$Cl$_2$: C, 69.93; H, 8.01. Found: C, 69.94; H, 8.03.

Preparation of 3,3-Ethylenedioxy-17α-hydroxy-21-methoxy-19-norpregna-5(10),9(11)-dien-20-one (14):

A suspension of the 3-ketal-17α,21-diol (13, 9.09 g, 24.27 mmol) in anhydrous 1,2-dimethoxyethane (DME) (200 mL; Aldrich, Sure-Seal) was stirred mechanically at ambient temperature under nitrogen. Proton Sponge (15.60 g, 72.81 mmol) was added as a solid, followed by the addition of trimethyloxonium tetrafluoroborate (10.77 g, 72.81 mmol). After stirring overnight, TLC (silica; 5% isopropanol in methylene chloride) indicated 60% conversion of starting material. A fourth equivalent of Proton Sponge (5.20 g, 24.27 mmol) was added as a solid, followed by the addition of a fourth equivalent of trimethyloxonium tetrafluoroborate (3.59 g, 24.27 mmol). After 3 hr at room temperature, all 21-hydroxy group was completely converted to the 21-methoxy, as evidenced by TLC. EtOAc and water were added to the mixture and the resulting mixture was transferred to a separatory funnel, and the organic and aqueous layers were allowed to separate. The organic layer was washed with ice-cold 1 N HCl (2×), water (1×), saturated NaHCO$_3$ (1×) and brine (1×). The combined EtOAc extracts (3×) were dried by filtration through sodium sulfate and evaporated in vacuo. The product obtained was dried overnight under high vacuum to give 9.34 g of a pale yellow foam (14) in 99.05% yield. Analysis of the foam 14 by TLC indicated virtually all PROTON SPONGE had been removed and the crude product was of sufficiently purity to carry directly on to the subsequent reaction. Approximately 200 mg of the product was purified by flash chromatography (5% isopropanol in methylene chloride) for analysis. Only the fractions of highest purity were combined and evaporated to recover a colorless film (14) in 131 mg. Trituration of the film produced a white powder (14). The powder was dried in vacuo at 80° C. to recover 98.2 mg of 14; m.p.= 117–119° C. FTIR (KBr, diffuse reflectance): $v_{max}$ 3470, 3025, 2924, 2816, 1707, 1473, 1448, 1420, 1360, 1268, and 1114 cm$^-$. NMR (300 MHZ, CDCl$_3$): δ 0.658 (s, 3 H, C18-CH$_3$), 3.443 (s, 3 H, C21-OCH3), 3.986 (s, 4 H, C3-OCH$_2$CH$_2$O—), 4.226 and 4.469 (AB, 2 H, C21-CH$_2$, J$_{AB}$=17.71 Hz) and 5.577 (br s, 1 H, C11-CH=). MS (EI) m/z (relative intensity): 388 (M$^+$, 58.4), 297 (48.6), 211 (57.4), 169 (53.9), 99 (100). Anal. Calcd for C$_{23}$H$_{32}$O$_5$.H$_2$O: C, 70.45; H, 8.33. Found: C, 70.42; H, 8.23.

Preparation of 3,3-ethylenedioxy-17α,20-dihydroxy-21-methoxy-19-norpregna-5(10),9(11)-diene (15):

To a solution of the 20-ketone (14, 9.34 g, 24.04 mmol) in dry THF (200 mL) was added LiAlH$_4$ (Aldrich, 1.0 M in ether, 48.08 mL, 48.08 mmol). After stirring ½ hr at room temperature under nitrogen, TLC (silica; 10% acetone in methylene chloride) indicated that all starting material had been converted to a an approximately 70:30 mixture of two more polar components. The reaction mixture was cooled to 0° C. and quenched by the addition of EtOAc (15–20 mL). After several min., saturated Na$_2$SO$_4$ solution (20 mL) was added carefully, followed by the addition of several scoops of solid Na$_2$SO$_4$. The mixture was allowed to stir for a period of 1 hr, then filtered through a Celite filter cake on a sintered glass funnel. The resulting filtrate was transferred to a separatory funnel, water and EtOAc were added, and the organic and aqueous layers were allowed to separate. The organic layer was removed, washed again with water, and then with brine. The combined EtOAc extracts (3×) were dried by filtration through sodium sulfate and evaporated in vacuo to recover a pale yellow foam. The foam was taken up in a minimum amount of ether (~20 mL) and small white crystals formed almost immediately. After allowing the ether mixture to stand overnight in the freezer, the ether was decanted. The crystals were washed with two additional portions of ether, then dried overnight under high vacuum to give 5.38 g of 15 as white crystals in 57.3% yield. Examination by TLC indicated that the crystals were exclusively the major product of the reaction.

A sample of analytical purity was obtained by recrystallization of 200 mg of white crystals 15 from a minimum amount of hot ether with a small amount of methylene chloride. The resulting white crystals were dried in vacuo at 56° C. to recover 115 mg of 15; m.p. 145–157° C. FTIR (KBr, diffuse reflectance): $v_{max}$ 3546, 3410, 3043, 2932, 2892, 2828, 1645, 1472, 1451, 1436, 1420, 1370, 1335, 1261, and 1108 cm$^{-1}$. NMR (300 MHZ, CDCl$_3$): δ 0.765 (s, 3 H, C18-CH$_3$), 3.395 (s, 3 H, C21-OCH3), 3.535 (dd, 1 H, C21-CH, J$_1$=9.76 Hz, J$_2$=3.00 Hz), 3.589 (dd, 1 H, C21-CH, J$_1$=9.76 Hz, J$_2$=6.15 Hz), 3.895 (dd, 1 H, C20-CH, J$_1$=6.15 Hz, J$_2$=3.00 Hz), 3.985 (s, 4 H, C3-OCH$_2$CH$_2$O—) and 5.599 (br s, 1 H, C11-CH=). MS (EI) m/z (relative intensity): 390 (M$^+$, 6.2), 372 (1.0), 314 (1.0), 297 (100), and 211 (42.6). Anal. Calcd for C$_{23}$H$_{34}$O$_5$: C, 70.74; H, 8.78. Found: C, 70.62; H, 8.78.

Preparation of 3,3-ethylenedioxy-5α,10α-epoxy-17α,20-dihydroxy-21-methoxy-19-norpregna-9(11)-ene (16):

To a solution of hexafluoroacetone trihydrate (4.28 g, 2.71 mL, 19.44 mmol) in methylene chloride (60 mL) was added solid Na$_2$HPO$_4$ (1.84 g, 12.96 mmol) and 30% H$_2$O$_2$ (2.92 mL, 28.51 mmol). The reaction mixture was stirred vigorously for a period of ½ hr at 4° C. (cold room). A chilled solution of the 17α,20-diol (15, 5.27 g, 12.96 mmol) in methylene chloride (30 mL) was added and rinsed in with additional methylene chloride (30 mL). After stirring overnight in the cold room, examination by TLC (silica; 15% acetone in methylene chloride) indicated that all starting material had been consumed. The epoxide product was evident in approximately a 75:25 (α:β) ratio.

The reaction mixture was transferred to a separatory funnel and washed successively with a 10% Na$_2$SO$_3$ solution (1×), water (1×), and brine (1×). The combined methylene chloride extracts (3×) were dried by filtration through sodium sulfate and evaporated in vacuo to recover a foam. Trituration with ether produced 3.63 g of an off-white solid (16) in 68.9% yield. Examination by TLC indicated that it was highly purified from the mother liquors.

A small sample (about 200 mg) was purified by flash chromatography (15% acetone in methylene chloride) for analysis. Fractions of the highest purity were combined and evaporated in vacuo to recover a white crystalline solid 16. The solid was recrystallized from a minimum amount of hot 15% acetone in methylene chloride and dried in vacuo at 80° C. to recover 76.5 mg of 16 as white crystals: m.p.= 173–185° C. FTIR (KBr, diffuse reflectance): $v_{max}$ 3536, 3466, 3040, 2970, 2932, 2905, 2872, 2812, 1475, 1456, 1426, 1373, 1344, and 1120 cm$^{-1}$. NMR (300 MHZ, CDCl₃): δ 0.764 (s, 3 H, C18-CH$_3$), 3.388 (s, 3 H, C21-OCH$_3$), 3.524 (dd, 1 H, C21-CH, J$_1$=9.91 Hz, J$_2$=3.00 Hz,), 3.577 (dd, 1 H, C21-CH, J$_1$=9.91 Hz, J$_2$=5.85 Hz,), 3.909 (s, 5 H, C3-OCH$_2$CH$_2$O— and C20-CH), and 6.062 (m, 1 H, C11-CH= of 5α,10α-epoxide). MS (EI) m/z (relative intensity): 406 (M$^+$, 0.9), 388 (3.1), 313 (34.0), 295 (47.9), 227 (30.5), 99 (100) and 87 (42.5). Anal. Calcd for C$_{23}$H$_{34}$O$_6$: C, 67.96; H, 8.43. Found: C, 67.76; H, 8.46.

Preparation of 3,3-ethylenedioxy-5α,17α,20-trihydroxy-11β-[4-(N,N-dimethylamino)phenyl]-21-methoxy-19-norpregn-9-ene (17):

A dry 250 mL 3-necked flask was equipped with a stirring bar, a reflux condenser, and two rubber septa. Magnesium (1.18 g, 48.5 mmol) was added and the entire apparatus dried further with a heat gun, under a stream of nitrogen. The apparatus was allowed to cool slightly and one crystal of iodine was added. After cooling completely, 20 mL of dry THF was added, followed by the addition of one drop of 1,2-dibromoethane. A solution of 4-bromo-N,N-dimethylaniline (8.81 g, 44.05 mmol) in THF (10 mL) was added via transfer needle and rinsed with additional THF (10 mL). The mixture was heated gently with a heat gun to reflux to initiate reaction (as evidenced by bleaching of color and consumption of magnesium) and then allowed to stir for a period of ½ hr at room temperature. Copper (I) chloride (480 mg, 4.85 mmol) was added as a solid and stirring was continued for a period of ½ hr. A solution of the epoxide (16, 3.58 g, 8.81 mmol) in THF (20 mL) was added via transfer needle and rinsed in with additional THF (10 mL). After stirring for another 2 hr. at room temperature, the reaction was quenched by the addition of saturated NH$_4$Cl solution (70 mL). Air was drawn through the mixture for period of ½ hr with vigorous stirring. The resulting mixture was transferred to a separatory funnel, and water and ether were added. The organic and aqueous layers were allowed to separate. The organic fraction was washed again with water (1×) and brine (1×). The combined ether extracts (3×) were dried by filtration through sodium sulfate and evaporated in vacuo to recover 7.7 g of a dark purple oil. The oil was filtered through a short bed of silica (125 g) on a sintered glass funnel. Elution with ether (4×200 mL) removed all of the aniline by-products. The product was eluted with EtOAc (8×100 mL). The EtOAc washes were evaporated in vacuo to recover a beige foam. Trituration with pentane produced a solid. The solid was dried overnight under high vacuum to give 2.48 g of 17 as a beige powder in 53.3% yield.

A small portion (250 mg) was purified by flash chromatography (5% isopropanol in methylene chloride) for analysis. Only fractions of the highest purity were combined and evaporated to recover a colorless gum. Trituration with pentane produced a solid. The sample was dried in vacuo at 80° C. to recover 56.9 mg of 17 as a white powder; m.p.=120–126° C. (softens). FTIR (KBr, diffuse reflectance): v$_{max}$ 3487, 2930, 1614, 1559, 1517, 1445, 1374, 1198, and 1120 cm$^{-1}$. NMR (300 MHZ, CDCl$_3$): δ 0.424 (s, 3 H, C18-CH$_3$), 2.908 (s, 6 H, —N(CH$_3$)$_2$), 3.361 (s, 3 H, C21-OCH$_3$), 3.461 (dd, 1 H, C21-CH, J$_1$=9.76 Hz, J$_2$=2.79 Hz), 3.527 (dd, 1 H, C21-CH, J$_1$=9.76 Hz, J$_2$=6.45 Hz), 3.783 (dd, 1 H, C20-CH, J$_1$=6.45 Hz, J$_2$=2.79 Hz ), 3.996 (m, 4 H, C3-OCH$_2$CH$_2$O—), 4.210 (d, 1 H, C11β-CH, J=8.70), 6.666 (d, 2 H, 3',5'-aromatic CH, J=8.70 Hz) and 7.093 (d, 2 H, 2',6'-aromatic CH, J=8.70 Hz). MS (EI) m/z (relative intensity): 527 (M$^+$, 15.1), 509 (14.6), 238 (6.2), 134 (32.4), 121 (100), and 99 (15.1). Anal. Calcd for C$_{31}$H$_{45}$NO$_6$.H2O: C, 69.77; H, 8.62; N, 2.62. Found: C, 69.80; H, 8.61; N, 2.43.

Preparation of 17α,20-dihydroxy-11β-[4-(N,N-dimethylamino)phenyl]-21-methoxy-19-norpregna-4,9-dien-3-one (18):

To a solution of the Grignard product (17, 2.13 g, 4.04 mmol) in THF (5 mL) was added glacial acetic acid (78.4 g, 75 mL, 1.31 mmol), followed by the addition of water (25 mL). The clear green solution obtained was allowed to stir overnight at room temperature under nitrogen. Examination by TLC (5% isopropanol in methylene chloride; over spotted with concentrated NH$_4$OH before developing) indicated that all starting material had been converted to a single, slightly less polar product. The reaction was cooled in an ice bath, then neutralized by the careful addition of concentrated NH$_4$OH (88 mL, 1.31 mmol) to a pH of 7.0 as indicated by a pH paper. The reaction mixture was transferred to a separatory funnel and extracted by methylene chloride (3×). The organic fractions were washed with water (1×) and brine (1×). The combined methylene chloride extracts were dried by filtration through sodium sulfate and evaporated in vacuo, and dried overnight under high vacuum to recover 1.93 g of an amber foam. Trituration of the amber foam with pentane produced a solid which was dried overnight under high vacuum to yield 1.78 g of 18 as a beige powder in 94.6% yield.

A small portion (~300 mg) of the above powder was purified by flash chromatography (15% acetone in methylene chloride) for analysis. Fractions containing the product were combined and evaporated to recover 223 mg of a yellow glass. Trituration of this yellow glass with pentane produced a solid. The solid was dried in vacuo at 80° C. to recover 185 mg of a pale yellow powder; m.p.=106° C. (softens). FTIR (KBr, diffuse reflectance): v$_{max}$ 3482, 2938, 1654, 1614, 1518, 1456, 1347, 1208, and 1125 cm$^{-1}$. NMR (300 MHZ, CDCl$_3$): δ 0.496 (s, 3 H, C18-CH$_3$), 2.911 (s, 6 H, —N(CH$_3$)$_2$), 3.381 (s, 3 H, C21-OCH$_3$), 3.485 (dd, 1 H, C21-CH, J$_1$=9.76 Hz, J$_2$=2.85 Hz), 3.547 (dd, 1 H, C21-CH, J$_1$=9.76 Hz, J$_2$=6.30 Hz), 3.805 (m, 1 H, C20-CH), 4.313 (d, 1 H, C11β-CH, J=7.20 Hz), 5.739 (s, 1 H, C4-CH), 6.660 (d, 2 H, 3',5'-aromatic CH, J=8.55 Hz) and 7.045 (d, 2 H, 2',6'-aromatic CH, J=8.55 Hz). MS (EI) m/z (relative intensity): 465 (M$^+$, 21.6), 372 (2.4), 134 (23.5), and 121 (10.0). Anal. Calcd for C$_{29}$H$_{39}$NO$_4$.H$_2$O: C, 73.67; H, 8.48; N, 2.96. Found: C, 73.64; H, 8.44; N, 2.91.

Preparation of 17α-hydroxy-11β-[4-(N,N-dimethylamino)phenyl]-21-methoxy-19-norpregna-4,9-diene-3,20-dione (10):

A suspension of 2-iodoxybenzoic acid (IBX, 599 mg, 2.14 mmol) in anhydrous dimethylsulfoxide (DMSO) (5.0 mL; Aldrich, Sure-Seal) was stirred magnetically under nitrogen and warmed in an oil bath at 55–60° C. After several minutes, all of the IBX was solubilized. To the IBX solution was added a solution of the 20-alcohol (18, 500 mg, 1.07 mmol) in DMSO (5 mL). Additional DMSO (3 mL) was used to rinse in residual 18. After a period ½ hr of reaction, approximately 70% of the 20-alcohol (18) had been converted to the 20-ketone (10), as evidenced by TLC (15% acetone in methylene chloride; aliquot was diluted in water and extracted by EtOAc). After 3 hr, there was no observable change in the conversion. The reaction mixture was transferred to a separatory funnel, diluted with water, and extracted by EtOAc (3×). The EtOAc extracts were washed with additional water (2×) and brine (1×). The combined extracts were dried by filtration through sodium sulfate, evaporated in vacuo, and dried overnight under high vacuum to recover 600 mg of a brown film. The film product was taken up in EtOAc and filtered through silica on a sintered glass funnel to remove residual DMSO and highly polar impurities. Evaporation of EtOAc afforded 450 mg of a yellow film. Repeated trituration with hexane, with scratching and sonicating, produced a solid. The solid was dried overnight under high vacuum to give 349 mg of 10 as a yellow powder in 70.1% yield. The product was carried directly to the next reaction without further purification. NMR (300 MHz, CDCl$_3$): δ 0.408 (s, 3 H, C18-CH$_3$), 2.906 (s, 6 H, —N(CH$_3$)$_2$), 3.454 (s, 3 H, C21-OCH$_3$), 4.245 and 4.388 (AB, 2 H, C21-CH$_2$, JAB=17.41 Hz), 4.378 (d, 1 H, C11β-CH, J=7.50), 5.758 (s, 1 H, C4-CH), 6.638 (d, 2 H, 3',5'-aromatic CH, J=8.55 Hz) and 6.975 (d, 2 H, 2',6'-aromatic CH, J=8.55 Hz).

Preparation of 17α-acetoxy-11β-[4-(N,N-dimethylamino)phenyl]-21-methoxy-19-norpregna-4,9-diene-3,20-dione (11):

A mixture of trifluoroacetic anhydride (47 mL) and glacial acetic acid (19.1 mL) in methylene chloride (300 mL) was allowed to stir at room temperature under nitrogen. After ½ hr of stirring, the mixture was cooled to 0° C. in an ice water bath and tosic acid (2.85 g, 14.98 mmol) was added. A solution of the 17α-hydroxy compound (10, 6.18 g, 13.33 mmol) was added in 50 mL of methylene chloride and rinsed in with additional CH$_2$Cl$_2$ (50 mL). After stirring for a period of 2 hr at 0° C., examination by TLC (silica; 10% acetone in methylene chloride; neutralized with NH$_4$OH before developing) indicated that the reaction was >95% complete. The reaction mixture was diluted with water (300 mL) and neutralized by careful addition of concentrated NH$_4$OH (75 mL). More NH$_4$OH was added to a pH of 7 as indicated by a pH paper. The product obtained was extracted by CH$_2$Cl$_2$ (3×) and the organic extracts were washed with water (2×) and brine (1×). The combined organic extracts were dried by filtration through Na$_2$SO$_4$ and evaporated in vacuo to give 7.13 g of the crude product (11). A pure material was obtained by flash column chromatography (silica; 10% acetone in methylene chloride). The impure fractions were combined and chromatographed a second time. The pure fractions from both chromatographic runs were combined and evaporated in vacuo, then evaporated from ether, and further dried under high vacuum to produce a pale yellow foam. Treatment with pentane followed by scratching and sonicating produced 4.13 g of 11 as a fine yellow powder in 61.3% yield; m.p. softens at 116° C.

Analysis by a reverse phase HPLC on a NOVAPAK™ C$_{18}$ column eluted with 70% CH$_3$OH in water with 0.03% Et$_3$N at a flow rate of 1 mL per min and at λ=302 indicated 98.87% purity of 11 with retention time $t_R$=6.45 min. FTIR (KBr, diffuse reflectance): $v_{max}$ 2940, 1734, 1662, 1612, 1518, 1446, 1370, 1235 and 1124 cm$^{-1}$. NMR (300 MHZ, CDCl$_3$): δ 0.38 (s, 3 H, C18-CH$_3$), 2.08 (s, 3 H, C17α-OAc), 2.90 (s, 6 H, —N(CH$_3$)$_2$), 3.42 (s, 3 H, C21-OCH$_3$), 4.07 and 4.33 (AB, 2 H, C21-CH$_2$, J$_{AB}$=18 Hz), 4.37 (s, 1 H, C11β-CH), 5.80 (s, 1H, C4-CH), 6.67 (d, 2 H, 3',5'-aromatic CH, J=9 Hz) and 7.0 (d, 2 H, 2',6'-aromatic CH, J=9 Hz). MS (EI) m/z (relative intensity): 505 (M$^+$, 13.5), 445 (1.1), 372 (2.7), 134 (16.2) and 121 (100). Anal. Calcd for C$_{31}$H$_{39}$NO$_5$: C, 73.64; H, 7.77; N, 2.77. Found: C, 73.34; H, 7.74; N, 2.70.

EXAMPLE 2

This Example further illustrates an embodiment of the process of the present invention.

Preparation of 17α-Hydroxy-21-chloro-19-norpregna-4,9-diene-3,20-dione (12):

The cyanohydrin (1, 250 g, 0.73 mol; Davos) was suspended in 3 L anhydrous THF (Aldrich) and stirred mechanically at room temperature under nitrogen. 4-(Dimethylamino)pyridine (DMAP) (22.35 g, 0.183 mol) was added as a solid. 138 mL (0.99 mol) of freshly distilled triethylamine (TEA) from BaO was added via an addition funnel over a period of about five minutes, followed by the addition of chloro(chloromethyl)dimethylsilane (115 mL, 0.876 mol). The reaction mixture was stirred overnight at ambient temperature. Thin layer chromatography (TLC)(on silica; 2% acetone in methylene chloride) showed that all the starting material had converted to the silyl ether. The reaction mixture was cooled to −78° C. in a dry ice/isopropanol bath and allowed to cool for about 30 minutes. Additional THF (500 mL) was added to rinse down the residue from the sides of the flask. Lithium diisopropylamide (LDA) (Acros; 2.0 M in THF/heptane, 1125 mL, 2.25 mole) was added dropwise to the reaction mixture via an addition funnel over a period of about 40 minutes. Upon completion of the addition, the reaction mixture was stirred for a period of 2 hours at −78° C. in a dry ice bath. 6 N HCl (3400 mL, 20.4 mol) was added via the addition funnel. Upon completion of the addition, the reaction mixture was allowed to warm to room temperature as the content of the bath evaporated. Stirring was continued overnight at room temperature under nitrogen. TLC (silica; 5% acetone in methylene chloride) indicated all silyl ether had converted to the 21-chloro compound (12). At this point the reaction mixture was a two-phase mixture with a large amount of precipitated material. The mixture was evaporated in vacuo to remove all volatile solvents, and chilled in an ice water bath. Ice water (about 4 L) was added and the mixture stirred vigorously. The precipitated product was collected by filtration on a Buchner funnel and washed with water (6× about 500 mL). After air drying for a period of several hours, the material was dried in vacuo at 40° C. over KOH for two nights. The resulting solid was transferred to an Erlenmeyer flask, suspended in pentane (about 2 L), and stirred vigorously for a period of 5–10 minutes. The resulting yellow powder was collected by filtration on a Buchner funnel and washed well with additional pentane (about 1 L). After air drying for a period of about one hour, the material was dried in vacuo at 35° C. over the weekend to recover 242.96 g of a yellow powder in 95.9% yield. This material was suitable to carry directly on to is the next reaction. m.p. 202–207° C. (191–193° C. after crystallization of a small portion from hot isopropanol and drying over toluene in vacuo). FTIR (KBr, diffuse reflectance): $v_{max}$ 3462, 2973, 2949, 2880, 1729, 1643, 1598, and 1572 cm$^{-1}$. NMR (300 MHZ, CDCl$_3$) δ 0.837 (s, 3H, C18-CH$_3$), 4.345 and 4.640 (AB, 2H, C21-CH$_2$, J$_{AB}$=16.81 Hz), 5.690 (s, 1H, C4-CH=). MS (EI) m/z (relative intensity): 348 (M$^+$, 100), 313 (33), 253 (67), 228 (54), 213 (72) and 91 (55).

Preparation of 17α-Hydroxy-21-acetoxy-19-norpregna-4,9-diene-3,20-dione (4):

A suspension of the 21-chloro compound (12, 241.96 g, 0.69 mol) and KOAc (137.41 g, 1.4 mol) in freshly opened acetonitrile (6 L) was stirred mechanically and brought to reflux under nitrogen. After 1.5 hours at reflux, TLC (silica; 5% acetone in methylene chloride) indicated that the reaction had gone to completion. The reaction mixture was allowed to cool to room temperature for a period of about 1.5 hours, following which it was evaporated in vacuo to near-dryness. The resulting material was rinsed in to the evaporating flask with acetone (about 500 mL) and acetone was evaporated. Ice water (2 L) was added and the flask was chilled in an ice bath. Additional water (about 3 L) was added and the mixture stirred vigorously for a period of about 10 minutes. The precipitated product was collected by filtration on a Buchner funnel and washed with additional water (4×500 mL). The product was allowed to air dry overnight on the Buchner funnel, and dried in vacuo overnight at 35° C. over KOH to obtain 237.28 g of the crude 21-OAc (4) as a pale yellow powder in 92.8% yield. The crude material was of sufficient purity to carry directly on to the hydrolysis. m.p. 209° C. (sinters) 210–218° C. (216–222° C. after crystallization of a small portion from boiling acetone and drying in vacuo over toluene). FTIR (KBr, diffuse reflectance): $v_{max}$ 3473.1, 2981.9, 2903.5, 2869.0, 1744.0, 1720.1, 1646.1, 1607.5 cm$^{-1}$. MS (EI) m/z (relative intensity): 372 (M$^+$, 86), 312 (75), 253 (100), 213 (93), 162 (76) and 91 (58).

Preparation of 17α-1-Dihydroxy-19-norpregna-4,9-diene-3,20-dione (5):

A suspension of the crude 21-acetate (4, 236.28 g, 0.63 mol) in freshly opened methanol (5 L) was deoxygenated by sparging with nitrogen for 30 minutes. A 1.0 M aqueous solution of KHCO$_3$ was similarly deoxygenated. The KHCO$_3$ solution (950 mL, 0.95 mol, 1.5×) was added to the steroid (4), and the suspension was stirred mechanically and brought to reflux under nitrogen. Several minutes after reaching reflux, a solution formed. After thirty minutes of holding the reaction at reflux, it was found by TLC (silica; 5% isopropanol in methylene chloride) that all starting material had converted to a single, more polar product. The reaction mixture was allowed to cool for a period of about one hour, and neutralized by the addition of HOAc (55 mL, 0.95 mol). The methanol was evaporated in vacuo to recover a yellow-brown slurry. Water was added (about 4 L) and the precipitated steroid allowed to stand overnight in the cold room (about 4° C.). The next morning, the product was collected by filtration on a Buchner funnel, washed well with water (4×500 mL) and allowed to air dry for a period of about 7 hours. After drying in vacuo at 35° C. over KOH over the weekend, 206.93 g of a yellow-brown solid was recovered in 100% yield. The crude diol (5) was carried directly on to the mono 3-ketal without purification. m.p. 165° C. (sinters) 174–189° C. (197–201° C. after crystallization of a small portion from a minimum amount of boiling methanol and drying in vacuo at 111° C.). FTIR (KBr, diffuse reflectance): $v_{max}$ 3518, 2943, 2864, 1713, 1655, and 1598 cm$^{-1}$. MS (EI) m/z (relative intensity): 330 (M+, 100), 271 (37), 253 (54), 228 (65), 213 (63), 74 (27) and 91 (43).

Preparation of 3,3-Ethylenedioxy-17α,21-dihydroxy-19-norpregna-5(10),9(11)-diene-20-one (13):

The crude 17α, 21-diol (5, 204.93 g, 0.62 mol) was suspended in methylene chloride (1 L, freshly opened) and stirred magnetically, at room temperature under nitrogen. Triethylorthoformate (258 mL, 1.55 mol, freshly distilled) was added, followed by ethylene glycol (181 mL, 3.24 mol). Tosic acid (5.9 g, 31 mmol) was added as a solid. Within several minutes of the addition, a homogenous solution formed, and the color had turned from amber to a dark black-green. After stirring the reaction mixture for a period of 30 minutes, it was found by TLC (silica; 50% isopropanol in methylene chloride) that all starting material had converted to the 3-ketal (13). The reaction mixture was quenched by the addition of an excess of NH$_4$OH (about 25 mL, 0.371 mol), and the methylene chloride was evaporated in vacuo. As the last traces of methylene chloride were removed, the product precipitated. Water (4 L) was added to the slurry and the mixture was stirred vigorously in an ice bath for one hour. The precipitated product was collected by filtration on a Buchner funnel, washed with water (5×500 mL) and air dried overnight on the funnel. The product was then dried in vacuo overnight at 35 C. over KOH to recover 233.87 g of a yellow solid (0.62 mol, 100%). The solid was suspended in ether (1.5 L), chilled in an ice bath, and stirred vigorously for a period of about 10 minutes. The resulting powder was collected by filtration on a Buchner funnel, washed with ice cold ether (3×500 mL), and allowed to air dry several hours. Inspection of the powder and the filtrate by TLC indicated the product had been significantly purified from the mother liquors. The product was dried in vacuo overnight at 35° C. to recover 193.45 g of the 3-ketal (13) in 83.9% yield as a beige powder. The overall purified yield from the cyanohydrin (1) was 74.7%. m.p. 199–209° C. (214–216° C. after crystallization of a small portion from a hot methylene chloride and drying in vacuo at 111° C. for analysis). FTIR (KBr, diffuse reflectance): $v_{max}$ 3481, 3394, 3046, 2922, 2880, 1714 and 1639 cm$^{-1}$. NMR (300 MHz, CDCl$_3$): δ 0.637 (s, 3H, C18-CH$_3$), 3.984 (s, 4H, C3-O CH$_2$CH$_2$O), 4.292 and 4.697 (AB, 2H, C21-CH$_2$, $J_{AB}$=19.51 Hz), 5.567 (t, 1H, C11-CH=, $J_{AVG}$=2.40 Hz). MS (EI) m/z (relative intensity): 374 (M$^+$, 52), 356 (21), 297 (35), 169 (55), 99 (99) and 86 (100). Anal. Calcd. For C$_{22}$H$_{30}$O$_5$·CH$_2$Cl$_2$: C, 69.93; H, 8.01. Found: C, 69.94; H, 8.03.

Preparation of 3,3-Ethylenedioxy-17α-hydroxy-21-methoxy-19-norpregna-5(10),9(11)-diene-20-one (14):

A suspension of the 3-ketal-17α, 21-diol (13, 192.74 g, 0.51 mol) in anhydrous DME (1900 mL; Aldrich, Sure-Seal) was stirred mechanically, at ambient temperature, under nitrogen. proton Sponge (437 g, 2.04 mol) was added as a solid, followed by trimethyloxonium tetrafluoroborate (about 300 g, 2.03 mol). After one hour, TLC (silica; 5% isopropanol in methylene chloride; an aliquot was diluted in water and extracted into ethyl acetate) indicated all 21-OH (13) had been converted to the 21-OCH$_3$ compound (14). The reaction mixture was quenched by the addition of methanol. After stirring 15 minutes, solids were removed by filtration through a sintered glass funnel and washed well with ethyl acetate (3×500 mL). Both the filtrate and the solids were examined by TLC (silica; 5% isopropanol in methylene chloride). The filtrate was a mixture of the 21-OCH$_3$ and proton Sponge, while the solids were exclusively proton Sponge. The filtrate was evaporated in vacuo at about 45° C. to recover a dark orange syrup. The orange syrup was cooled in an ice bath and cold 1N HCl (4 L, chilled overnight in the cold room) was added with vigorous stirring. Initially, the steroid precipitated as a gum, but continued stirring and scraping afforded a solid. The solid was collected on a Buchner funnel, washed with additional 1N HCl (4×500 mL), then with water (4×500 mL) to a pH of about 6 by means of the pH paper. Examination by TLC indicated the steroid still contained a trace of proton Sponge. The solid was again suspended in cold 1N HCl (2 L) and stirred in an ice bath for 30 minutes. The product was collected on a Buchner funnel, washed with additional cold 1N HCl (4×500 mL), then water (6× about 500 mL) to a pH of about 6 (pH paper). Proton Sponge was effectively removed as evidenced by TLC. The product was allowed to air dry, and further dried overnight in vacuo at 40° C. over KOH to recover 182.25 g of a pale yellow powder in 92.2% yield. The crude 21-OCH$_3$ compound (14) was of sufficient purity to carry directly on to the subsequent reduction. m.p. 92–94° C. (sinters) 102–107° C. (117–119° C. after purification of a small portion by flash chromatography (5% isopropanol in methylene chloride) for analysis). FTIR (KBr, diffuse reflectance): $v_{max}$ 3424, 3034, 2931, 2889, 2837, 1721, 1642, and 1472 cm$^-$. NMR (300 MHz, CDCl$_3$): δ 0.653 (s, 3H, C18-CH$_3$), 3.441 (s, 3H, C21-OCH$_3$), 3.986

(s, 4H, C3-OCH₂CH₂O), 4.225 and 4.480 (AB, 2H, C21-CH₂, J$_{AB}$=17.71 Hz), 5.576 (m, 1H, C11-CH=). MS (EI) m/z (relative intensity): 388 (M+, 58), 297 (49), 211 (57), 169 (54), and 99 (100). Anal. Calcd. For C$_{23}$H$_{32}$O$_5$·H$_2$O: C, 70.45; H, 8.33. Found: C, 70.42; H, 8.23.

Preparation of 3,3-Ethylenedioxy-17-α,20-dihydroxy-21-methoxy-19-norpregna-5(10), 9(11)-diene (15):

To a stirred solution of 20-ketone (14, 181.25 g, 0.47 mol) in anhydrous THF (900 mL), LiAlH₄ (Aldrich, 1.0 M in ether; 235 mL, 235 mmol) was added via an addition funnel over for a period of approximately ½ hr. Immediately upon completion of the addition, examination by TLC (silica; 10% acetone in methylene chloride) indicated all starting material had been converted to ~ a 3:1 mixture of the two 20-alcohols (7). The reaction mixture was cooled to 0° C. and quenched by a careful addition of ethyl acetate (235 mL) over a period of about 5 minutes. The reaction mixture was further quenched by the addition of saturated Na₂SO₄ solution (235 mL) over a period of about 5 minutes. Solid Na₂SO₄ (150 g) was added and the suspension stirred one hour. Precipitated aluminum salts were removed by filtration through a Celite filter cake on a sintered glass funnel. The solids were washed with ethyl acetate (3×500 mL), and the filtrate evaporated in vacuo to recover a syrup. The flask was chilled in an ice bath and water (2 L) was added, thereby obtaining in a gummy mass. Additional water (3 L) with vigorous stirring and scraping gave no improvement. THF (1 L) was added to help break up the mass, but did not afford a solid precipitate. The mixture was transferred to a separatory funnel and extracted with methylene chloride (3×2 L). The organic fractions were washed again with water (1×), then brine (1×). The combined methylene chloride fractions were dried by filtration through sodium sulfate, evaporated in vacuo, and dried briefly under high vacuum to recover a foam (196.9 g). Trituration with ether afforded 107.81 g of a pale yellow solid in three crops in 59.6% yield. The solid (15) was almost exclusively the major isomer. Only a trace of the minor isomer was present as evidenced by TLC. m.p. 142° C. (sinters) 148–153° C. (145–147° C. after crystallization of a small portion from a minimum amount of hot ether and a small amount of methylene chloride and drying in vacuo at 56° C. for analysis). FTIR (KBr, diffuse reflectance): v$_{max}$ 3544, 3417, 3038, 2931, 2827, 1644, 1621 cm⁻¹. NMR (300 MHz, CDCl₃): δ 0.765 (s, 3H, C18-CH₃), 3.395 (s, 3H, C21-OCH₃), 3.535 (dd, 1H, C21-CH, J₁=9.61 Hz, J₂=3.00 Hz), 3.589 (dd, 1H, C21-CH, J₁=9.61 Hz, J₂=6.15 Hz), 3.895 (m, 1H, C20-CH), 3.984 (s, 4H, C3-O CH₂CH₂O), 5.592 (m, 1H, C11-CH=). MS (EI) m/z (relative intensity): 390 (M+, 6), 372 (1), 314 (1), 297 (100) and 211 (43). Anal. Calcd for C$_{23}$H$_{34}$O$_5$: C, 70.74; H, 8.78. Found: C, 70.62; H, 8.78.

All references cited herein, including patents, publications, and patent application, are hereby incorporated in their entireties by reference.

While this invention has been described with an emphasis upon several embodiments, it will be obvious to those of ordinary skill in the art that variations of the embodiments may be used and that it is intended that the invention may be practiced otherwise than as specifically described herein. Accordingly, this invention includes all modifications encompassed within the spirit and scope of the invention as defined by the following claims.

What is claimed is:

1. A process for preparing a compound of formula 10 comprising selectively oxidizing the 20-hydroxyl group of the compound of formula 18

2. The process of claim 1, wherein the selective oxidation is carried out by treating the compound of formula 18 with o-iodoxybenzoic acid.

3. A process for preparing a compound of formula 11 comprising (a) providing a compound of formula 13

(b) selectively methylating the 21-hydroxyl group of the compound of formula 13 to obtain a compound of formula 14

14

(c) reducing the 20-ketone group of the compound of formula 14 to obtain a compound of formula 15

15

(d) epoxidizing the compound of the formula 15 to obtain a 5α,10α-compound of formula 16

16

(e) introducing a N,N-dimethylaminophenyl group at the axial 11-position via a conjugate addition and concomitant opening the epoxide ring of the compound of formula 16 to obtain a compound of formula 17

17

(f) deketalizing the compound of formula 17 to obtain a compound of formula 18

18

(g) selectively oxidizing the 20-hydroxyl group to a ketone group to obtain a compound of formula 10

10 and (h) acetylating the compound of formula 10 to obtain the compound of formula 11.

4. The process of claim 3, wherein the epoxidation is carried out by treating the compound of formula 15 with hexafluoroacetone and hydrogen peroxide in the presence of a weak base.

5. The process of claim 3 including trituration of the resulting crude product of the compound of formula 16 with an ether.

6. The process of claim 3, wherein the introduction of the N,N-dimethylaminophenyl group at the 11β-position with the concomitant opening of the epoxide ring of the compound of formula 16 is carried out by treating the compound of formula 16 with a Grignard reagent in the presence of a cuprous halide, quenching the Grignard reaction mixture with an ammonium salt, and oxidizing the cuprous halide to cupric halide.

7. The process of claim 3, wherein the selective oxidation of the 20-hydroxyl group is carried out by treating the compound of formula 18 with o-iodoxybenzoic acid.

8. The process of claim 3, wherein the acetylation of the compound of formula 10 is carried out by treating the compound with trifluoroacetic anhydride, acetic acid, and p-toluenesulfonic acid.

* * * * *